United States Patent [19]
Schwartz

[11] Patent Number: 5,749,874
[45] Date of Patent: May 12, 1998

[54] CARTILAGE REPAIR UNIT AND METHOD OF ASSEMBLING SAME

[75] Inventor: Robert E. Schwartz, Manhasset, N.Y.

[73] Assignee: Matrix Biotechnologies, Inc., Melville, N.Y.

[21] Appl. No.: 774,390

[22] Filed: Dec. 30, 1996

Related U.S. Application Data

[63] Continuation of Ser. No. 659,174, Jun. 5, 1996, abandoned, which is a continuation-in-part of Ser. No. 384,849, Feb. 7, 1995, Pat. No. 5,632,745.

[51] Int. Cl.$^6$ ................................................. A61B 17/68
[52] U.S. Cl. ........................... 606/75; 606/77; 606/215
[58] Field of Search .............................. 606/75, 72, 60, 606/77, 76, 80, 88, 96, 99, 100, 104, 213, 215, 219; 623/16, 20

[56] References Cited

U.S. PATENT DOCUMENTS

| | | | |
|---|---|---|---|
| 4,873,976 | 10/1989 | Schreiber | 606/213 |
| 4,884,572 | 12/1989 | Bays et al. | 606/139 |
| 4,895,148 | 1/1990 | Bays et al. | 606/213 |
| 5,059,206 | 10/1991 | Winters | 606/213 |
| 5,067,964 | 11/1991 | Richmond et al. | 623/18 |
| 5,246,441 | 9/1993 | Ross et al. | 606/53 |

OTHER PUBLICATIONS

Acufex brochure entitled "Surgical Technique for Suretac" 1991, 12 pages, author unknown, Dec. 1991.
Pagnani et al. "Arthroscopic Shoulder Stabilization" Op Tech in Sports Med, vol 1, No. 4, pp. 276–284, Oct. 1993.
Warner et al. "Arthroscopic Bankart . . . Device" Op. Tech. in Sports Med. vol. 1, No. 2, pp./ 192–198, Apr. 1991.
Stuart, "Treatment of Chronic Chondral Injuries" Sports Med and Arth, vol. 2, No. 1, pp. 50–58, Dec. 1994.

*Primary Examiner*—Guy V. Tucker
*Attorney, Agent, or Firm*—Amster, Rothstein & Ebenstein

[57] ABSTRACT

A method of assembling an improved bio-absorbable cartilage repair system includes the step of directly inserting the insert into a cavity in the delivery unit so as to leave a top of the insert exposed. A flexible, porous fabric piece, consisting substantially of bio-absorbable material, is then applied over the exposed top of the inserted insert and through a plurality of the windows of the delivery unit sidewall. The fabric piece includes a central body portion configured and dimensioned to substantially cover the exposed top of the inserted insert, and a plurality of leg portions extending outwardly from the body portion, the leg portions being configured and dimensioned to fit through the windows. Substantially all of each leg portion is next pulled through a respective window to cause the body portion to deform the inserted insert into assuming the shape of the cavity therebelow. Finally, the leg portions projecting from the windows are trimmed. The remaining fabric piece retains the inserted insert within the delivery unit. Preferably, the pulling also causes the body portion to deform the exposed top of the inserted insert into assuming a desired shape or contour.

13 Claims, 7 Drawing Sheets

FIG.7
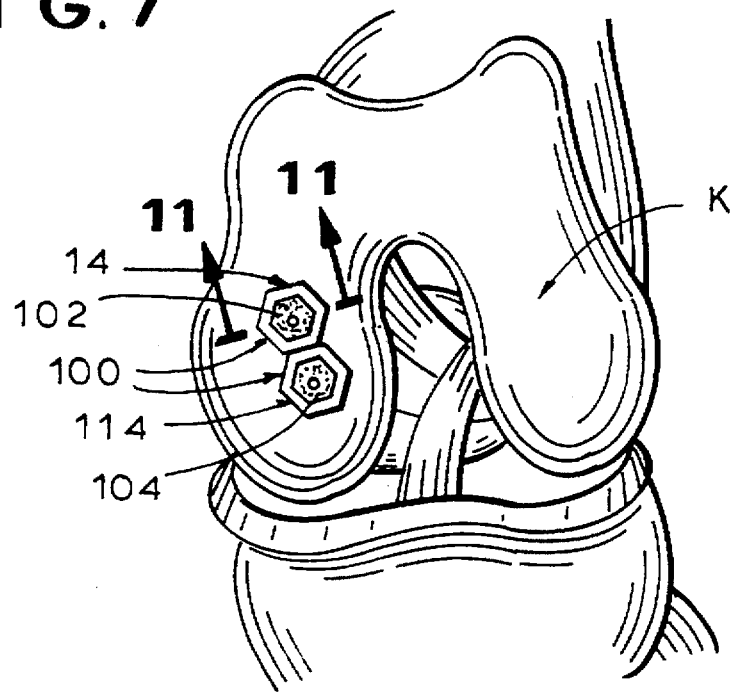
FIG.8
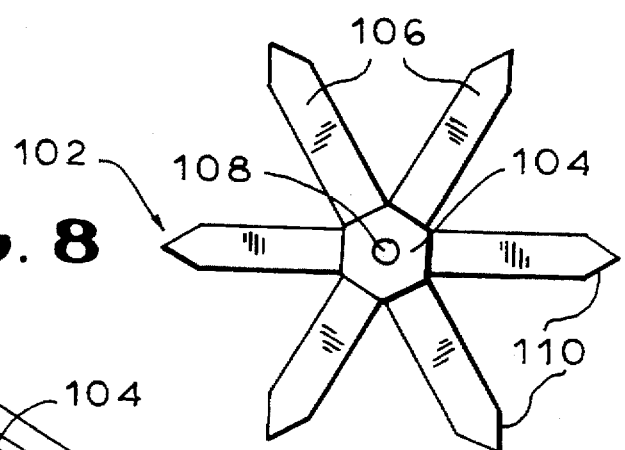
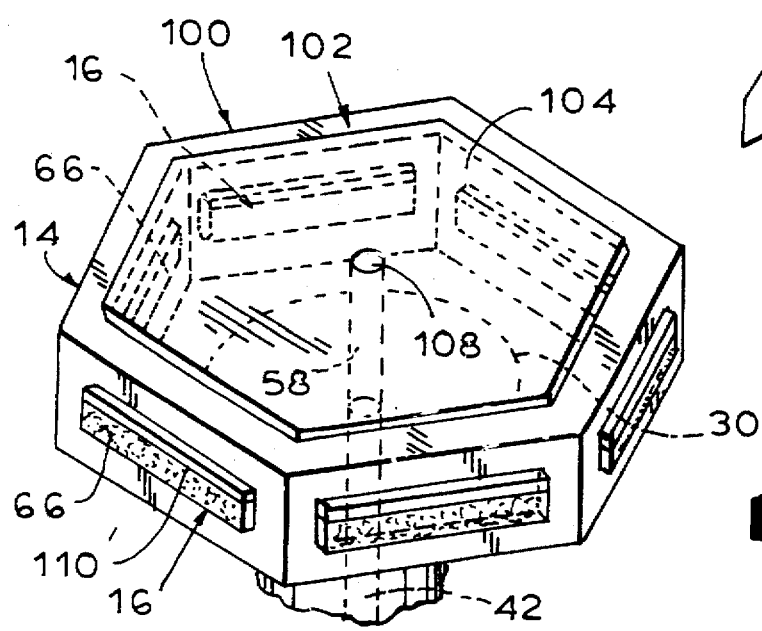
FIG.10

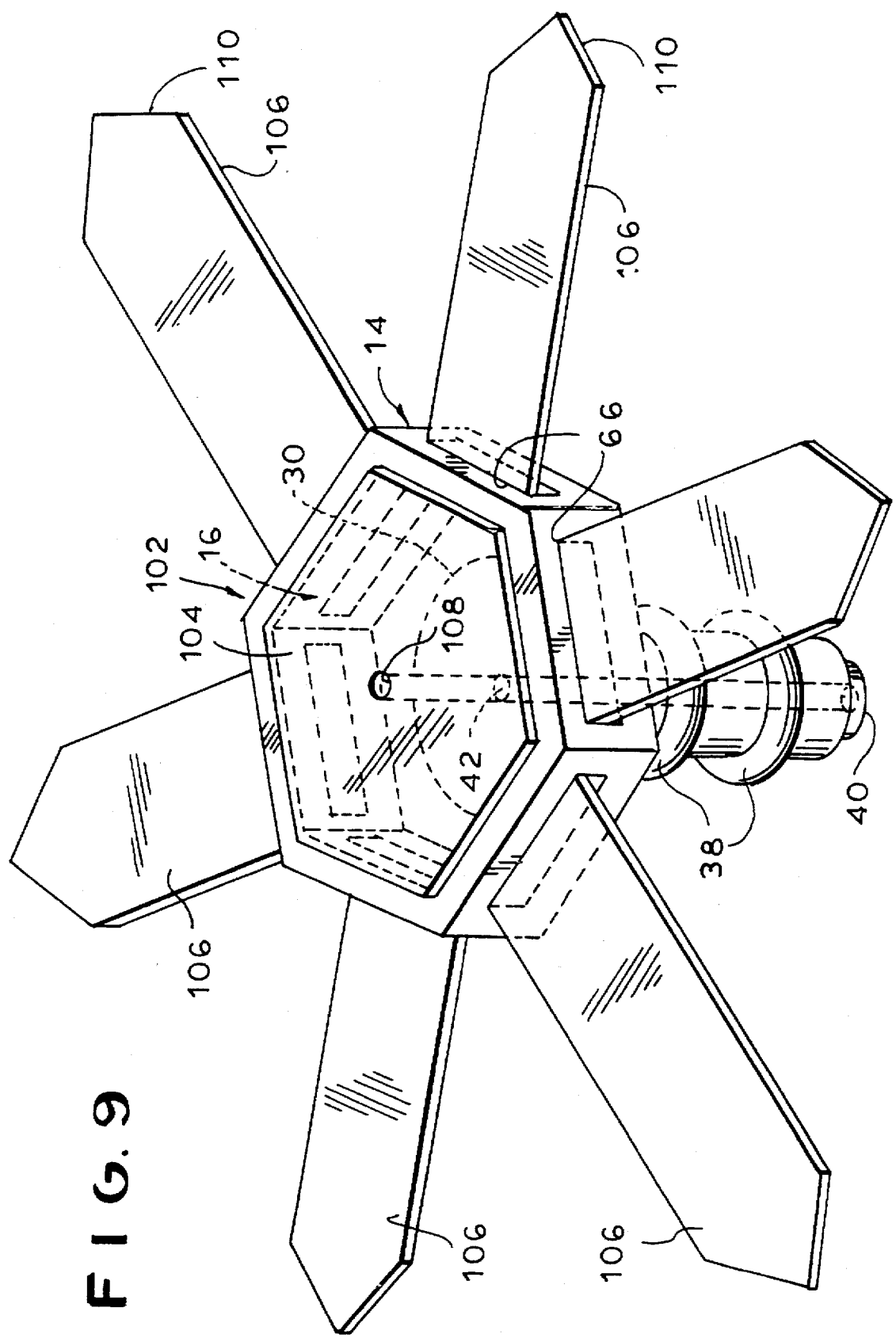

CARTILAGE REPAIR UNIT AND METHOD OF ASSEMBLING SAME

CROSS-REFERENCE TO RELATED APPLICATION

This is a continuation of application Ser. No. 08/659,174 filed on Jun. 5, 1996, now abandoned, which is a CIP of application Ser. No. 08/384,849 filed on Feb. 7, 1995, now U.S. Pat. No. 5,632,745.

BACKGROUND OF THE INVENTION

This invention relates to a bio-absorbable cartilage repair system for regenerating articular cartilage and, more particularly, a system which allows for vascular invasion and cellular migration between the system and the adjacent healthy area of articular cartilage and cancellous bone, thereby resulting in regeneration of the damaged articular cartilage. More specifically, the present invention relates to such a bio-absorbable cartilage repair system and to a method of assembling the same.

Articular cartilage on the surface of bones in joints, most particularly the knee and hip joints, is susceptible to deterioration caused by injury or disease. This deterioration of cartilage leads to severe pain and eventually loss of joint movement. As a result, various methods have been developed to treat and repair damaged or destroyed articular cartilage.

Prosthetic devices are often used to replace damaged or destroyed articular cartilage. For example, U.S. Pat. No. 4,627,853 discloses prosthesis which are used for articular cartilage replacement. The prosthesis are prepared by demineralization of a bone segment, the demineralized bone segment serving as a replacement for articular cartilage.

U.S. Pat. No. 4,880,429 discloses a prosthetic meniscus which is implanted in the knee. The prosthetic meniscus acts as a scaffold for regrowth of native meniscal tissue, and comprises collagen fibers interspersed with glycoaminoglycan molecules.

U.S. Pat. No. 5,176,710 discloses a prosthesis for replacing bone material on the articulating surface of a joint. The prosthesis has a specific modulus of elasticity so as to confer stiffness to the prosthesis, and contains concave shapes which are suitable for biologic ingrowth.

U.S. Pat. No. 4,502,161 discloses a prosthetic meniscus which replaces the natural meniscus between the articular surfaces of the bones and the joints, and comprises an insert and extension for attachment to the bone and a reinforcing fabric or mesh embedded therein.

U.S. Pat. No. 3,745,590 discloses a prosthesis for the repair or replacement of joints, which prosthesis comprises a body portion, including a stem and ligamentous elements, and allows for tissue ingrowth.

U.S. Pat. No. 5,123,927 discloses a knee prosthesis comprising bone cement containing an antibiotic.

Although there are several prosthetic devices which can be used in the replacement of damaged or destroyed articular cartilage, prosthetic devices have several disadvantages. For example, cements which are used to attach prosthetic devices to bones may loosen and eventually fail. In addition, fragmented cement can move into the joints and associated lymph tissue and cause inflammation and further damage. Further, cements result in the formation of fibrous tissue between the bone and the prosthesis. Another major disadvantage associated with the use of prosthesis is that the prosthetic device may be larger than the damaged cartilage that needs to be replaced, thereby requiring removal of portions of healthy bone and/or cartilage in order to accommodate the prosthetic device. Hence, the need remains for a system for repairing and regenerating articular cartilage which avoids the problems associated with prosthetic devices.

Another means used to treat damaged articular cartilage is the placement of repair pieces onto the bone, which repair pieces substitute for cut-out pieces of cartilage. For example, U.S. Pat. No. 5,067,964 discloses an articular cartilage repair piece which comprises a layer of non-woven, felted fibrous material which is limp and readily conformable to flat and curved surfaces. The articular cartilage repair piece is attached to the bone, for example, by bio-absorbable screws or pins or like temporary fixation techniques. Fibrous tissue ingrowth eventually surrounds the repair piece, thereby causing the repair piece to be permanently attached to the bone. Although U.S. Pat. No. 5,067,964 discloses an alternative method for repairing damaged articular cartilage, it does not disclose any means or method of regenerating damaged or destroyed articular cartilage.

Quite recently, U.S. patent application Ser. No. 08/289,387, filed Aug. 12, 1994, disclosed a basic system for regenerating damaged or destroyed articular cartilage, wherein the regenerated articular cartilage is functionally similar to non-damaged articular cartilage.

Referring now to FIGS. 1–6 of the drawing thereof, and in particular to FIG. 1 thereof, therein illustrated is the basic cartilage repair system described in the aforementioned application, generally designated by the reference numeral 10. More particularly, the cartilage repair system 10 illustrated in FIG. 1 is comprised of a plurality of assemblies generally designated 12 (two being illustrated, but it being understood that the requisite number is determined by the extent of the damaged area). Each assembly 12 is in turn comprised of a bio-absorbable delivery unit 14 and a porous bio-absorbable insert 16. The delivery unit 14 is configured and dimensioned to be mounted in both the area from which damaged or destroyed articular cartilage has been removed and the adjacent healthy cancellous bone area of the bone. The porous insert 16 is supported by and in the delivery unit 14 and establishes communication between the removed area (that is, the area from which the damaged or destroyed articular cartilage has been removed) and the adjacent healthy area for a chondrogenic growth-supporting matrix, thereby promoting vascular invasion and cellular migration to achieve articular cartilage regeneration. For bio-absorbability, both components 14, 16 are preferably ceramic-free.

While the system 10 is illustrated in FIG. 1 as being used to regenerate damaged or destroyed articular cartilage on the femoral knee joint surface K, those skilled in the medical arts will readily appreciate that the system 10 is, equally useful in other articular joints such as the shoulder, hip, and the like. The extent of the damaged or destroyed articular cartilage on the surface of the bone will determine whether the system 10 employs a single assembly 12 or a plurality of assemblies 12. The illustrated assemblies 12 (and in particular the delivery units 14 thereof) are polygonal in plan and interfitting—that is, disposed such that they preferably can be mounted in contiguous abutting contact in a side-to-side relationship. The polygonal nature of the periphery of the assemblies permits interfitting of the assemblies 12 (as generally illustrated in FIG. 6) and is thus preferred where a plurality of the assemblies 12 are to be used to completely cover a designated area of the bone. However, where only a single assembly 12 will be used, other configurations, such as a circular configuration, may be preferred.

While theoretically it might be possible to create in a single manufacturing operation a unitary, one-piece, integral assembly 12 which performs the functions of both the delivery unit 14 and the insert 16, two separate and independently formed components are preferably utilized—namely, the delivery unit 14 and the insert 16. As will be discussed below in detail, the insert 16 can be made of a relatively wide variety of different materials and may even include a repair factor (such as a growth factor or an attachment factor) releasably disposed therein to assist in establishing the chondrogenic growth-supporting matrix. Accordingly, the two-component nature of the assembly 12 enables the insert 16 to be selected from a supply of different inserts 16 at the time of surgery so as to meet the particular needs of the patient at the time with regard to both the basic composition of the insert 16 and any repair factor composition therein. Again, because of the differing natures of the insert 16 (and any repair factors therein) and its delivery unit 14, it may be necessary for particular types of inserts 16 to be stored before use in different environments from the delivery units 14—for example, in order to provide appropriate preservation of the repair factor. Finally, the delivery unit 14 and insert 16 of an assembly 12 must have different functional characteristics which would be difficult to achieve through known manufacturing techniques in an integral, one-piece, unitary element. Thus, as will be discussed below, the delivery unit 14 must have sufficient strength and integrity (i.e., dimensional stability) to enable it to be tamped into the bone without significant bending or deforming, while the insert 16 is preferably a flexible and resilient porous material in the form of a matrix to enable it to be interconnected with the delivery unit 14 and thereby provide a chondrogenic growth-supporting matrix positioned by the delivery unit 14.

Referring specifically to FIGS. 2 and 5, delivery unit 14 is comprised of an upper cup-like support frame 22 and a lower T-like elongate member 23. The support frame 22 has an upper rim 24 defining an open top, side walls 26 and a bottom portion 30. The elongate member 23 (which is preferably cylindrical) extends downwardly from the bottom portion 30 (which is preferably concave) and has radially extending ribs 38, a blunt bevelled bottom 40 and a bore 42 (preferably about 1.5 mm in diameter) extending axially there through. The disc or waferlike insert 16 has a top surface 52, side walls 54, a bottom surface 56 and a bore 58 (preferably about 1.5 mm in diameter) extending axially therethrough and after insertion into delivery unit 14 coaxial with bore 42 thereof.

The support frame 22 of the delivery unit 14 receives the insert 16 therein, with the side walls 26 of the support frame 22 receiving therewithin the side walls 54 of the insert 50. The bottom surface 56 of the insert 16 and the bottom portion 30 of the support frame 22 are correspondingly shaped, preferably with the bottom surface of the insert 16 defining a protrusion and the upper surface of the bottom portion 30 defining a protrusion-receiving cavity, so that the two bores 42, 58 are automatically and accurately coaxially disposed after the insertion process. In other words, when the insert 16 is secured in the supporting frame 22, the bore 42 through the elongate member 23 and the bore 58 through the insert 16 are in vertically aligned contiguous relationship.

As will readily be appreciated by those skilled in the implant arts, if vascular invasion and cellular migration is to be effected between the healthy cancellous bone area and the area of removed damaged cartilage via the insert 16, means must be provided to preclude relative rotation of the delivery unit 14 and the insert 16. This may be accomplished in a number of different ways.

First, as best seen in FIGS. 2–3 and 6, the external periphery of the insert 16 and the internal periphery of the support frame 22 may be polygonal or irregular (that is, non-circular) and sized to abut one another so that they are locked together for rotation only as a unit. For example, as illustrated, the hexagonal outer periphery of insert 16 snugly fits within hexagonal inner periphery of support frame 22 to preclude relative rotation. This is a preferred mechanism for use in conjunction with the flanges 64/windows 66 mechanism to be described hereafter.

Second, the upper surface of the concave bottom portion 30 of the support frame 22 may define upwardly extending bosses 60 adjacent the side walls 26, while the lower surface of the insert 16 may define upwardly extending recesses 62 configured and dimensioned to receive the bosses 60, as best seen in FIGS. 3 and 6. When a boss/recess system is employed, the number of bosses 60 and recesses 62, as well as the shape, size and placement thereof, are selected so that, when the insert 16 is within the delivery unit 14, the bosses 60 are snugly received in the recesses 62, such that the insert 16 and delivery unit 14 are precluded from relative rotation as long as the insert 16 is within the support frame 22. This system of bosses 60 and recesses 62 is not preferred.

Third, in all embodiments the side walls 54 of the insert 16 define radially outwardly extending flanges 64 therein or therethrough, and the side walls 26 of the support frame 22 define windows 66 therethrough configured and dimensioned to snugly receive the flanges 64 therein or therethrough. The number of flanges 64 and windows 66, as well as the size, shape and spacing thereof, are selected so that, when the insert 16 is within the support frame 22, relative rotation of the insert 16 and the delivery unit 14 is precluded as long as the flanges 64 snugly extend into (and possibly through) the windows 66. In order to enable the insert 16 with its flanges 64 to be easily inserted into the supporting frame 22 with its windows 66, the insert 16, or at least the flanges 64 thereof, are preferably resiliently flexible. The flanges 64 or windows 66 may also have bevelled edges to facilitate snapping the flanges 64 into the windows 66 during the insertion process. Alternatively, the flanges 64 may be formed in situ after insertion of insert 16 into support frame 22.

In the last two cases, the height of the bosses 60 and the depth of the recesses 62 or the relative heights of the flanges 64 and windows 66 are selected so that the bottom surface 56 of the insert 16 will rest on the upper surface of the bottom portion 30 of the delivery unit 14. It will be appreciated by those skilled in the mechanical arts that a wide variety of different keying mechanisms well known in the mechanical arts may be used in order to preclude relative rotation of the insert 16 and the delivery unit 14. However, it must be kept in mind that, over time, the bio-absorbable elements—that is, the delivery unit 14 and the insert 16—will be disappearing as the human body hydrolyzes the material from which they are made. Accordingly, the selection of an appropriate keying mechanism to preclude relative rotation of the insert 16 and the delivery unit 14 must be made with this consideration in mind. It will be appreciated that while, for the purposes of exposition, a variety of different keying mechanisms have been illustrated in a single embodiment, in fact a single keying mechanism—namely, the windows 66/flanges 64 mechanism which is always present—may suffice for a particular embodiment, although a plurality of such mechanisms may also be used.

In order to enable the insert 16 to function as a chondrogenic growth-supporting matrix, it must have access to vascular invasion and cellular migration to regenerate the articular cartilage defect. Such access is provided on the internal periphery of the insert 16 by the bore 58. On the external periphery of the insert 16, the windows 66 on the supporting frame 22 provide direct contact to the adjacent healthy articular cartilage or to the adjacent repair assemblies. These windows 66 allow cellular migration to occur to the insert. The entire top surface 52 of the insert 16 is exposed to the articular environment of the affected joint, and a substantial portion of the bottom surface 56 of the insert 16 is exposed to the cancellous bone through channels 68, which extend axially through the bottom 30 of support frame 22. Providing communication between the area of removed damaged articular cartilage and the healthy cancellous or trabecular bone, the number of the channels 68, as well as the size, shape and placement thereof, is selected to provide a desirable level of communication without unduly deleteriously affecting the strength of the delivery unit 14. The axially disposed channels 68 are, of course, disposed radially outwardly of the elongate member 23 so that the channels 68 do not have to extend axially therethrough.

The delivery unit 14 is hard and preferably does not bend or deform under expected pressures. It is preferably integrally molded. It is critical that the delivery unit 14 be made of a bio-absorbable material such as those well known in the implant art. For example, it is preferably ceramic-free and made of polyglycolic acid, polylactic acid or combinations thereof (e.g., co-polymers and mixtures thereof). The delivery unit 14 is preferably dimensionally stable in its intended environment and neither shrinks nor expands except through bio-absorption.

Several dimensionally stable delivery units 14 can be placed contiguously in an area of removed damaged articular cartilage such that a large portion of the removed area will be filled with the assemblies 12. In this case, the delivery units 14 are preferably regular polygons and interfitting in an abutting and contiguous relation. A circular delivery unit may be used where only one delivery unit is employed or where only partial coverage of the removed area is desired.

The insert 16 is made substantially of porous material in the form of a matrix or sponge, preferably defining at least 95% voids by volume, so that it can serve as a biological scaffold for an invasion of cells to regenerate the articular cartilage. It typically has the felt-like feel of a non-woven fabric. The insert 16 may be manually bendable or flexible when it is necessary to push, press or snap the same into the delivery unit 14. It is critical that the insert 16 consists substantially (typically at least 99% by weight) of a ceramic-free bio-absorbable material selected from the group consisting of hyaluronic acid (e.g. as a fiber matrix), polyglycolic acid (e.g., as fiber matrix), collagen, including type I collagen (e.g., as a sponge matrix), polylactic acid (e.g. as a fiber matrix), fibrin clot (which can be filled and molded into the delivery unit), collagen gel (which can be overlayed into a polyglycolic acid matrix), isolated periosteal cells, polydioxane, polyester, alginate or combinations thereof. The polylactic acid, and to a lesser degree the hyaluronic acid, polyglycolic acid (PGA), and alginate, contribute to the hardness and longevity (i.e., life in situ after implantation) of the insert 16. The insert may be annealed (i.e., heat-treated or cooked) to modify its crystallinity and thus its hardness and longevity. The isolated periosteal cells may be cultured in the insert material or overlaid at the time of surgery into the insert material. Other cell types, such as mesenchymal stem cells or chondrocytes, may also be added to the insert material.

In addition, preferably the insert 16 contains within the matrix "repair factors" such as growth factors and/or attachment factors well known in the medical arts. For example, the insert 16 can contain, as growth factors, fibroblast growth factor (acidic or basic), transforming growth factor-beta (1, 2, 3 or one of the members of the supergene family of TGF-beta, such as bone morphogenic protein; BMP), insulin, insulin-like growth factor 1 & 2, platelet-derived growth factor or combinations thereof. The attachment factors which can be used in the insert include fibronectin, RGD polypeptide and combinations thereof. Typically, the repair factors total less than 1% by weight of the insert, but can range up to 10% depending on the factors' specific activities and release kinetics. The repair factors may be chemically combined with the basic implant composition (e.g., during polymerization thereof) or may be added to an already formed basic implant composition. In the former case, additional repair factor will typically become available as the basic implant composition biodegrades.

Referring now to FIG. 5, after surgical removal of the damaged or destroyed articular cartilage, the elongate member 23 (extending downwardly from the concave bottom portion 30 of the support frame 22) is placed into the cancellous bone 74 through the subchondral bone plate 72 which is below the damaged articular cartilage area. The support frame 22 is supported by the subchondral bone plate 72. The elongate member 23 has a blunt bevelled bottom 40 so that the elongate member 23 can be placed easily into the cancellous bone 74, which is a soft region of the bone, while still creating frictional retention of the elongate member. The bottom 40 of the elongate cylindrical member 23 is blunt so that the bottom 40 does not break when the elongate cylindrical member 23 is placed inside the cancellous bone 74. When the elongate member 23 is placed into the soft cancellous bone 74, the cancellous bone 74 is displaced by, and reforms around, the radially extending ribs 38 of the elongate member 23. In this manner, the elongate member 23, and thereby the entire cartilage repair system 10, is held in place.

When the delivery unit 20 is placed in the bone, the upper rim 24 of the support frame 22 is flush with undamaged articular cartilage 76. The windows 66 and the upper rim 24 of the support frame 22 are not placed inside the bone, but rather remain exposed to the surrounding articular cartilage. The top surface 52 of the polymer insert 50 is exposed to the joint space environment. The top portion of the exterior surface of the side walls 26 of the support frame 22 laterally abuts either the top portion of the exterior surface of the side walls 26 of adjacent support frames 22 (see FIG. 6), or undamaged peripheral articular cartilage 76 when placed adjacent to an area of removed cartilage. The bottom portion of the exterior surface of the side walls 26 of the support frame 22 (i.e., the portions below windows 66) rests on and laterally abuts the subchondral bone plate 72.

When the cartilage repair system is placed in an area of removed damaged articular cartilage, through the subchondral bone plate 72 into the cancellous bone 74, the channels 68 in the bottom portion 30 of the support frame 22 allow for communication between the healthy cancellous bone 74 and the damaged articular cartilage area via a chondrogenic growth-supporting matrix. This permits vascular invasion and cellular migration, which results in regeneration of the articular cartilage. The regenerated articular cartilage is functionally similar to undamaged articular cartilage. The cartilage repair system of the invention is bio-absorbed over time and therefore need not be surgically removed during or after cartilage regeneration. The absorption rate is formula controlled and can range from 6–12 weeks to one year depending on its site-specific application.

As the basic bio-absorbable composition of the insert 16 degrades or hydrolyzes over time, any repair factors contained therein are progressively released into the site, thus further promoting cellular regeneration. Cellular regeneration occurs throughout the insert.

U.S. patent application No. 08/384,849 discloses preferred methods for surgically implanting the unit in a patient.

The term "bio-absorbable" is used in the specification and claims hereof to indicate a material which will be degraded or absorbed by the body such that regenerated articular cartilage thereabout is functionally similar to non-damaged articular cartilage.

As noted above, while it is conceivable to present the surgeon with a pre-assembled cartilage repair system (wherein the delivery unit already has inserted thereinto the insert), there are good and sufficient reasons for providing the surgeon with the separate components and allowing him (or a surgical nurse) to form the assembly. However, assembly of the components into the cartilage repair system has not proven to be as easy and as rapid as might be desired. Loosely positioning the insert in the unit cavity and then applying downward pressure on the top of the insert typically suffices to dispose most of the insert within the cavity of the delivery unit. However, the insert sometimes fails to extend all the way up to and at least partially through the windows, as is preferred in order to achieve good communication between the insert and the cancellous bone for regenerating articular cartilage via the windows. Finally, while the upper surface of the insert is preferably slightly convexly curved (or otherwise curved to provide a contoured joint surface), the use of fingers to apply pressure to the upper surface, in order to properly dispose the insert within the delivery unit cavity, does not lend itself to such a smoothly convex (or otherwise curved) upper surface for the insert.

Accordingly, it is an object of the present invention to provide an improved multi-component cartilage repair system which enables a simple and rapid assembly of the various components.

Another object is to provide such an improved system which can be easily and rapidly assembled at the last moment in the operating theater.

A further object is to provide such an improved system which enables the insert to be assembled in the delivery unit with a desired upper surface contour and with the insert extending to and through the windows of the delivery unit.

It is also an object of the present invention to provide a method for assembling such an improved system.

SUMMARY OF THE INVENTION

It has now been found that the above and related objects of the present invention are obtained in an improved bio-absorbable cartilage repair system for regenerating damaged or destroyed articular cartilage on a surface of a bone by establishing a chondrogenic growth-supporting matrix between an area of damaged or destroyed articular cartilage that has been removed and an adjacent healthy area of articular cartilage and cancellous bone. The system comprising an assembly of a delivery unit, an insert and a fabric piece.

The dimensionally stable, ceramic-free, bio-absorbable delivery unit defines an open top cavity and is configured and dimensioned to be mounted in both an area of damaged or destroyed articular cartilage that has been removed and an adjacent healthy area of articular cartilage and cancellous bone. The deformable, ceramic-free, porous, bio-absorbable insert is supported by and in the cavity of the delivery unit so as to leave a top of the insert exposed and establishes communication between the removed area and the adjacent healthy area for a chondrogenic growth-supporting matrix. The delivery unit cavity has an open top, a bottom and a sidewall connecting the top and bottom, the sidewall defining a plurality of windows to which the insert extends to allow cellular migration to the sides of the insert by an adjacent healthy area of articular cartilage.

The flexible, porous fabric piece consists substantially of bio-absorbable material disposed over the exposed top of the insert and through a plurality of the windows of the delivery unit sidewall. The fabric piece includes a central body portion configured and dimensioned to substantially cover the exposed top of the insert and a plurality of leg portions extending outwardly from the body portion, the leg portions having free ends extending through respective windows. The body portion assumes the shape of the cavity therebelow. Thus the fabric piece retains the insert within the delivery unit.

In a preferred system, the leg portions extend beyond the respective windows by 1–2 mm, and the fabric piece is formed of fibers of a substantially bio-absorbable material which is the same as the bio-absorbable insert. Preferably the fabric piece is spider-shaped, the body portion thereof completely covers the exposed top of the insert, and the plurality of leg portions is equal in number to the plurality of windows.

The present invention further encompasses a method of assembling such an improved bio-absorbable cartilage repair system. The method comprises the steps of directly inserting the insert into a cavity in the delivery unit so as to leave a top of the insert exposed. A flexible, porous fabric piece, consisting substantially of bio-absorbable material, is then applied over substantially the entire exposed top of the inserted insert and through a plurality of the windows of the delivery unit sidewall. The fabric piece includes a central body portion configured and dimensioned to completely cover the exposed top of the inserted insert, and a plurality of leg portions extending outwardly from the body portion, and the leg portions being configured and dimensioned to fit through the windows. Substantially all of each leg portion is next pulled through a respective window to cause the body portion to deform the inserted insert into assuming the shape of the cavity therebelow. Finally, the leg portions projecting from the windows are trimmed. The remaining fabric piece retains the inserted insert within the delivery unit.

Preferably, the pulling also causes the body portion to deform the exposed top of the inserted insert into assuming a desired shape or contour.

BRIEF DESCRIPTION OF THE DRAWING

The above brief description, as well as further objects, features and advantages of the present invention, will be more fully understood by reference to the following detailed description of the presently preferred, albeit illustrative, embodiments of the present invention when taken in conjunction with the accompanying drawings wherein:

FIG. 7 is a fragmentary schematic view of a knee having therein a pair of assemblies of the improved repair system;

FIG. 8 is a top plan view of a fabric piece useful in the present invention;

FIG. 9 is an exploded isometric view of the improved cartilage repair system of the present invention in an intermediate stage of assembly;

FIG. 10 is an isometric view of one assembly of the improved cartilage repair system after trimming;

DETAILED DESCRIPTION OF THE PREFERRED EMBODIMENTS

Figure 1:
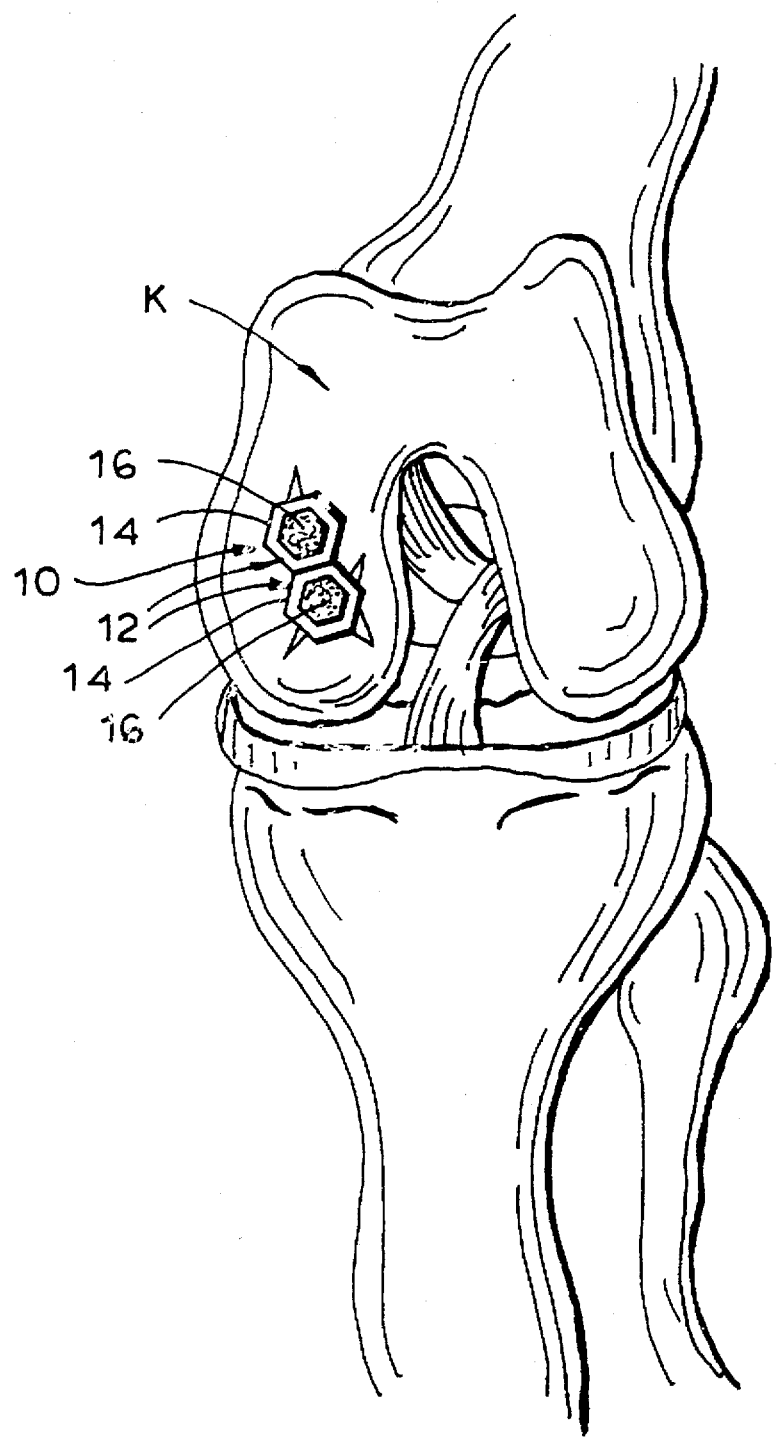
FIG. 1 is a fragmentary schematic view of a knee having therein a pair of assemblies of the prior art cartilage repair system.
Figure 2:
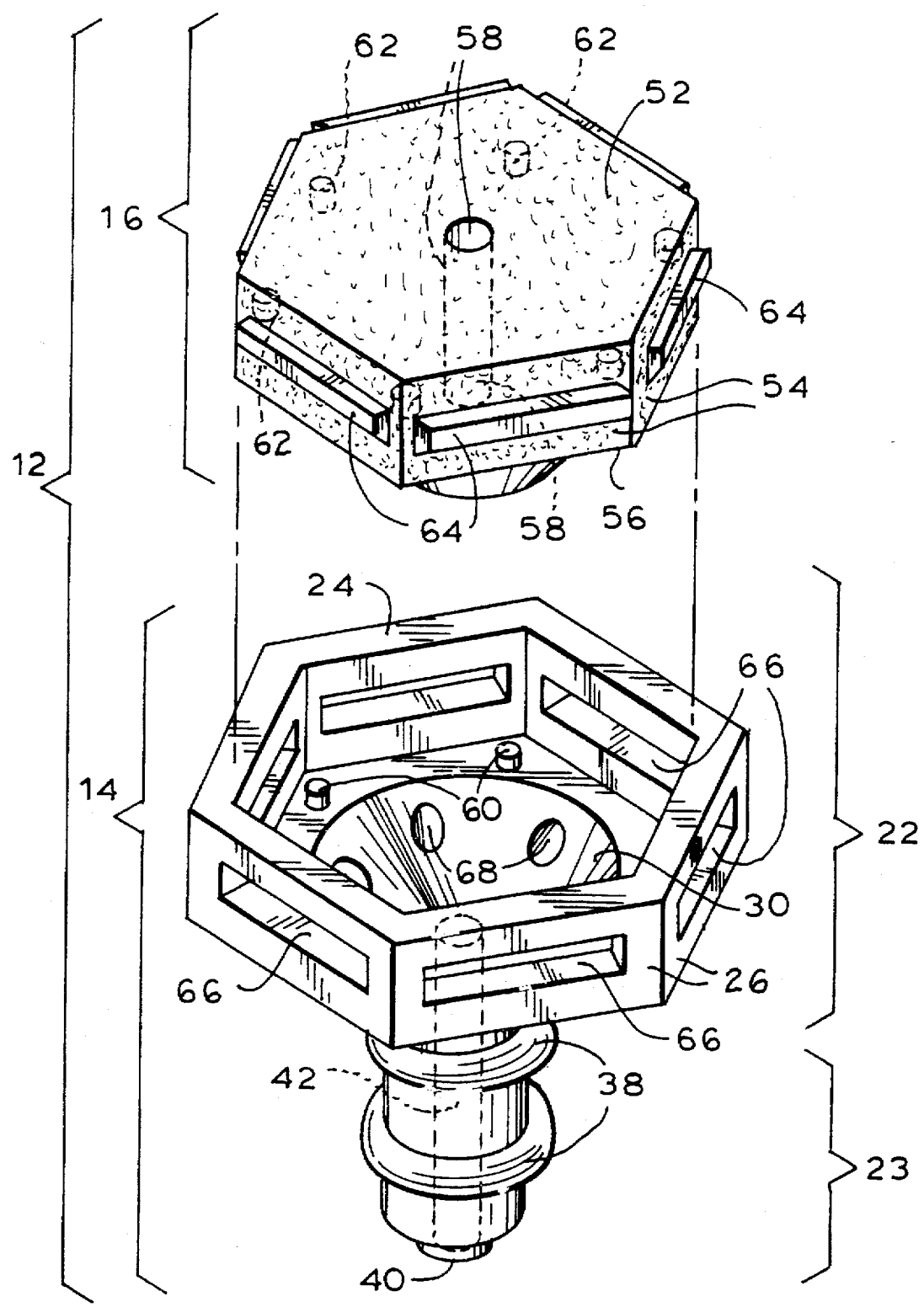
FIG. 2 is an exploded isometric view of one assembly of the prior art cartilage repair system.
Figure 3:
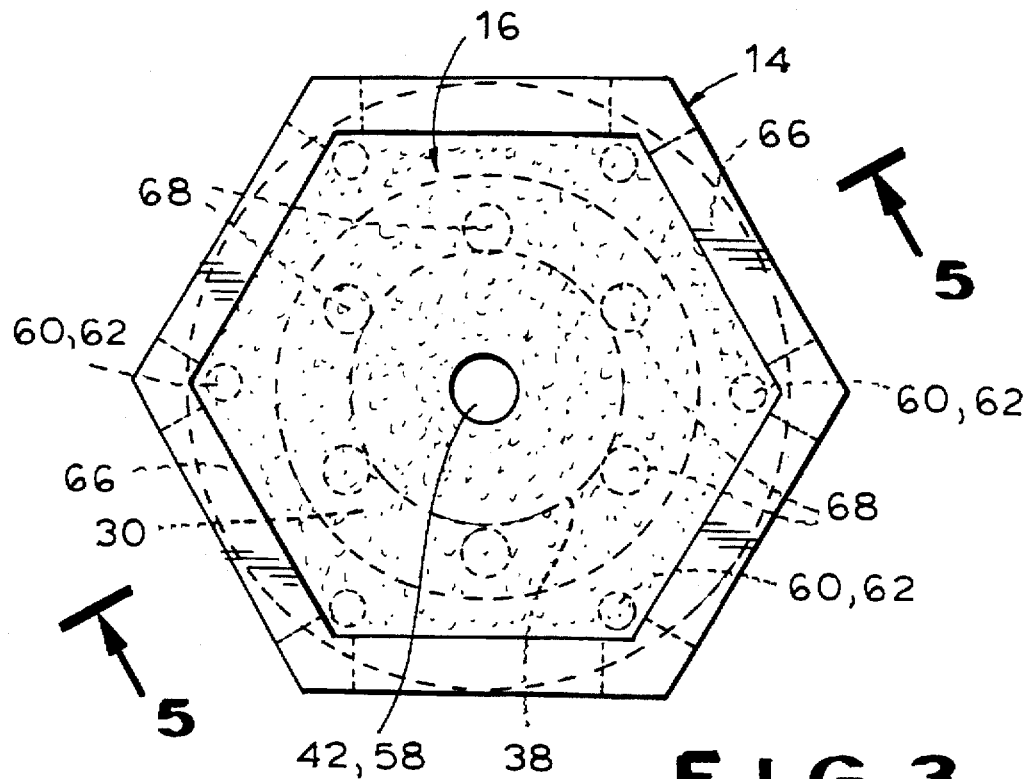
FIG. 3 is a top plan view thereof.
Figure 4:
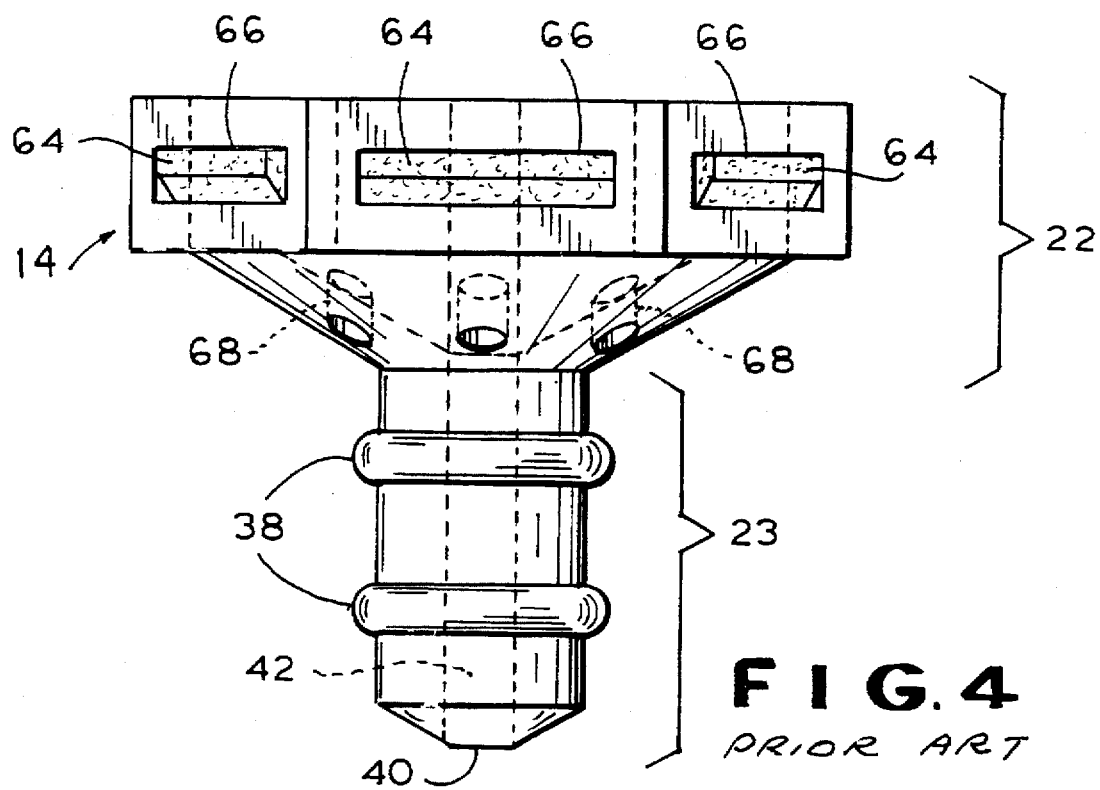
FIG. 4 is a side elevational view thereof.
Figure 5:
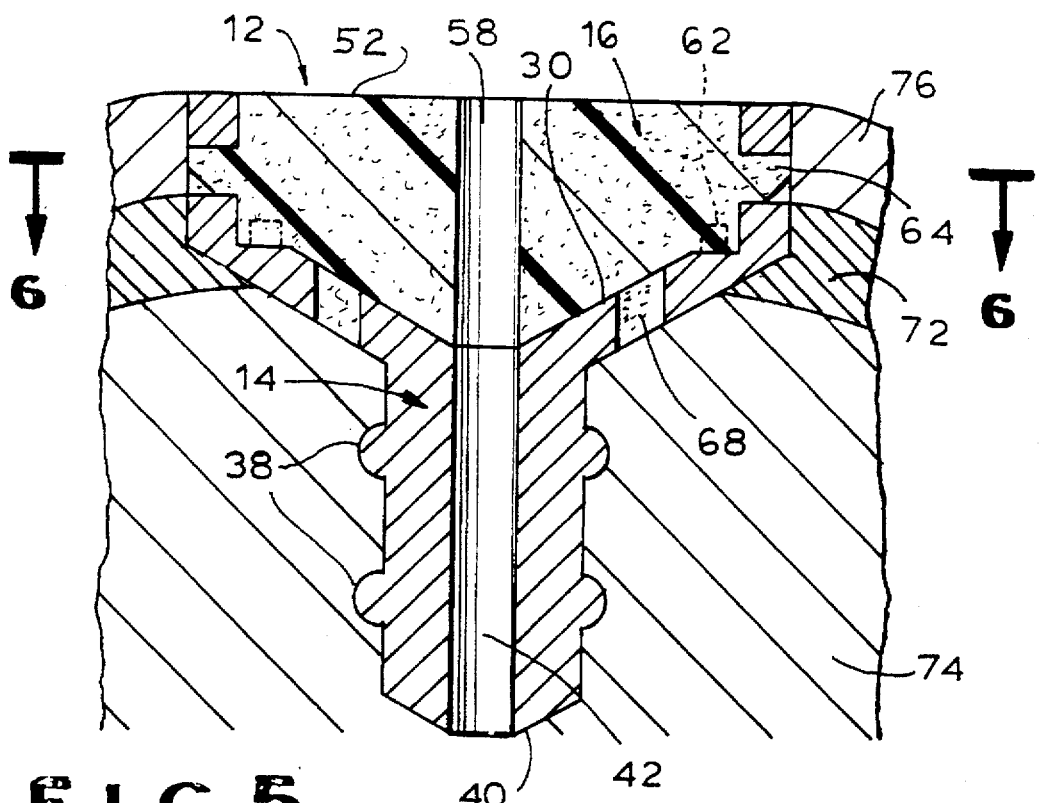
FIG. 5 is a sectional view thereof taken along line 5—5 of FIG. 3 and fragmentarily shows the cartilage repair system inserted into a bone.
Figure 6:
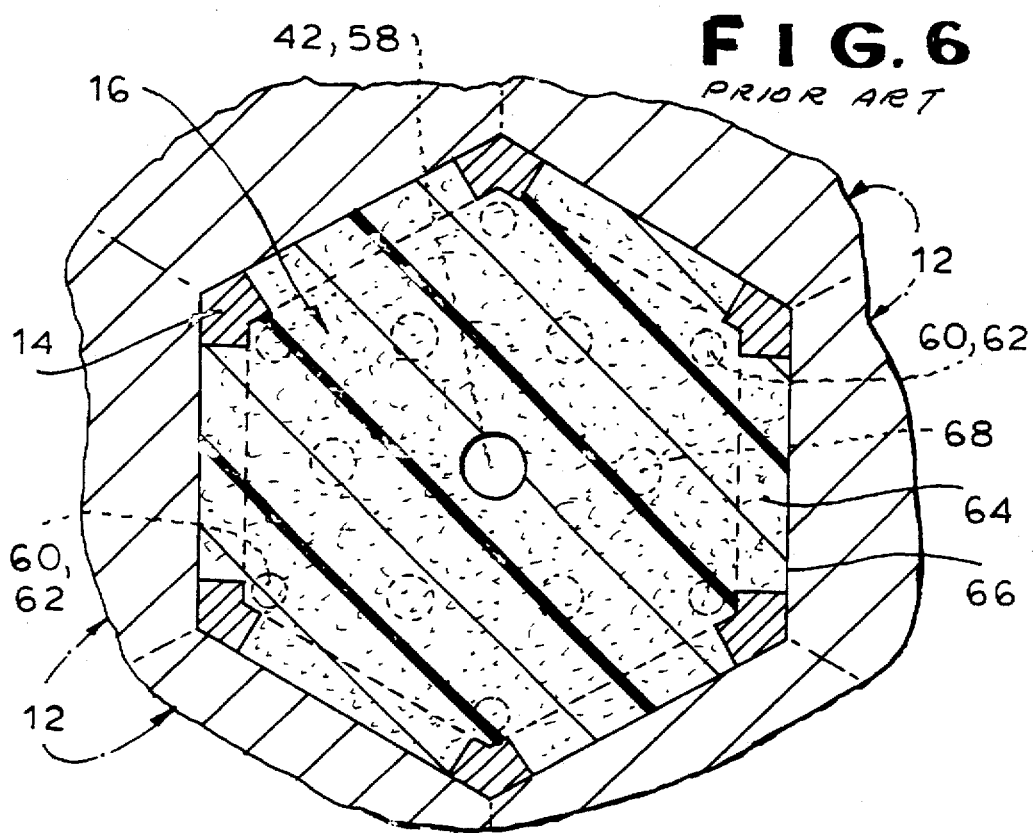
FIG. 6 is a sectional view thereof taken along line 6—6 of FIG. 5, with potential adjacent assemblies being fragmentarily illustrated in phantom line.

Comparing the illustration of the improved cartilage repair system of the present invention in FIG. 7 with the illustration of the basic cartilage repair system in FIG. 1, it will be appreciated that the present invention, generally designated 100, additionally includes a flexible, porous fabric piece, generally designated 102. The fabric piece 102 consists substantially of bio-absorbable material (typically at least 99% by weight bio-absorbable) and is ceramic-free. The fabric piece may be woven or non-woven, but is preferably thin and porous to facilitate the establishment of communication between the insert therebelow and the removed area and/or the adjacent healthy area on the other side of the fabric piece. The fabric piece 102 may be formed of fibers of a substantially bio-absorbable material which is the same as the bio-absorbable insert 16. It is preferably felt-like. A preferred material for use is a non-woven porous mat, 1 mm thick, 95% voids by volume, formed of polyglycolic acid (PGA) and available from Albany International of Mass. The mat is preferably platen-pressed on one side—namely, the side that will face away from the insert 16.

As illustrated in FIG. 8, the fabric piece 102 is spider-shaped and includes a central body portion 104 configured and dimensioned to completely cover the exposed top of the insert 16 when the insert is appropriately positioned within the delivery unit 14, and a plurality of leg portions 106 extending outwardly from the body portion 104. The plurality of leg portions 106 is equal in number to or less than the plurality of windows 66 in the delivery unit 14, six such leg portions 106 and six such windows 66 being illustrated. Each leg portion 106 has a free end 110 which extends through a respective window 66 and beyond by about 1–2 mm. Preferably, the transverse dimension of the free end 110 is less than the transverse dimension of the window 66 through which it extends in order to facilitate placement of the free end 110 through the window 66. The body portion 104 of the fabric piece 102 substantially covers the top of the insert 16 and conforms to the contour of the insert top (although, as will be noted below, it is the body portion 104 which shapes the insert top). The body portion 104 and adjacent segments of the leg portions 106 generally assume the interior shape of the cavity of the delivery unit 14 at least adjacent the sidewall of the delivery unit cavity above the windows 66. Thus, once the fabric piece 102 is disposed over the exposed top of the insert 16 and through a plurality of the windows 66 of the delivery unit sidewall, the fabric piece 102 retains the insert 16 within the delivery unit 14, especially by virtue of the extension of the fabric piece leg portions 106 through the windows 66.

It will be appreciated that, when the fabric piece 102 has N leg portions 106, a polygonal central body portion 104 of the fabric piece 102 is preferably correspondingly shaped with N sides.

Prior to trimming (as described hereinafter), the free ends of the leg portions 106 typically end in points to facilitate their insertion through the respective windows 66. Once the leg portions have been inserted and trimmed to 1–2 mm beyond the respective windows 66, there is no further need for a point on the free ends thereof.

The central body portion 104 of fabric piece 102 additionally defines an aperture 108 therethrough. The aperture 108 is intended to be aligned with the bore 42 through the elongate member 23 and the bore 58 through the insert 16 so as to receive a guidewire therethrough. This facilitates use of the guidewire for insertion of the insert 16 into the delivery unit 14 and placement of the fabric piece 102 over the insert 16 and through the windows 66 of the delivery unit 14. However, alternatively, either or both of the inserts 16 and the fabric piece 102 may be devoid of a bore 58 or aperture 108, respectively, during the assembly process. In this instance, the guidewire can later be inserted through the fabric piece 102 and the inserted insert 16 and into the bore 42 of elongate member 23. The compositions of the insert 16 and fabric piece 102 lend themselves well to such insertion of a guidewire and, after the guidewire has been removed, tend to retain the bore or aperture thus formed.

Again because of the composition of the insert 16 and the fabric piece 102, it unnecessary for the insert 16 to be formed with flanges 64 designed to fit through respective windows 66 of the delivery unit 14.

Rather, as will be described below, the flanges 64 or the equivalent thereof are automatically formed during the assembly of the improved cartilage repair system.

Figure 11:
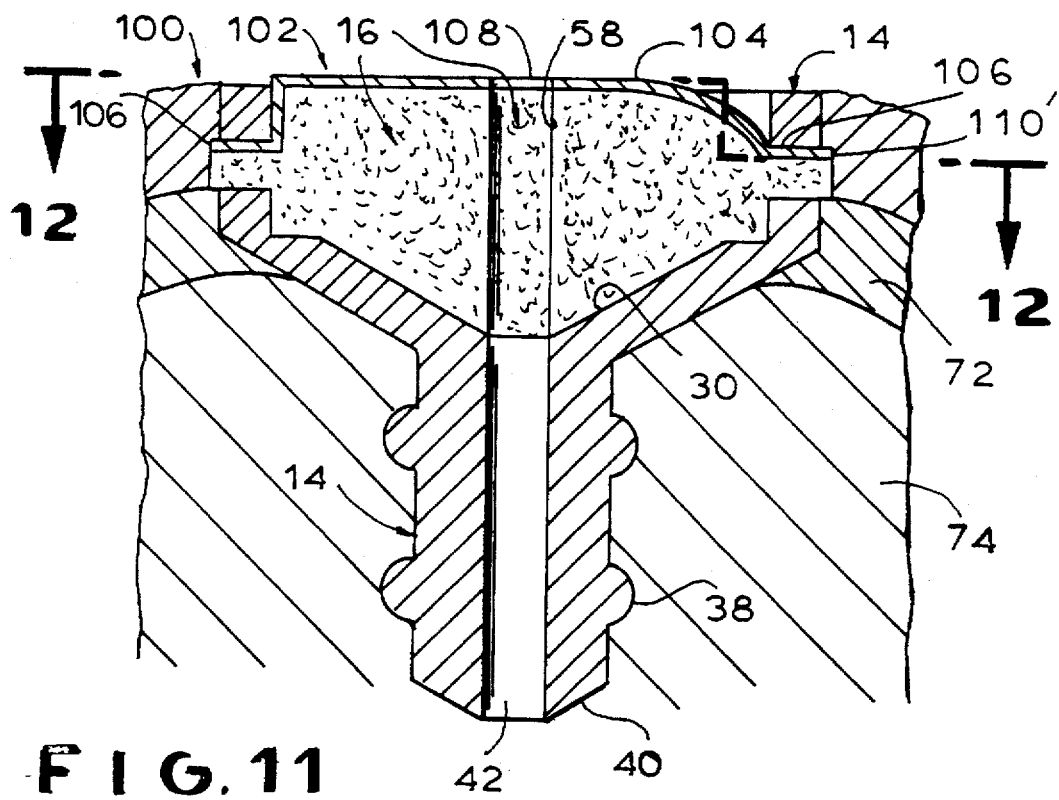
FIG. 11 is a fragmentary sectional view taken along line 11—11 of FIG. 7 and fragmentary shows the improved cartilage repair system inserted into a bone.
Figure 12:
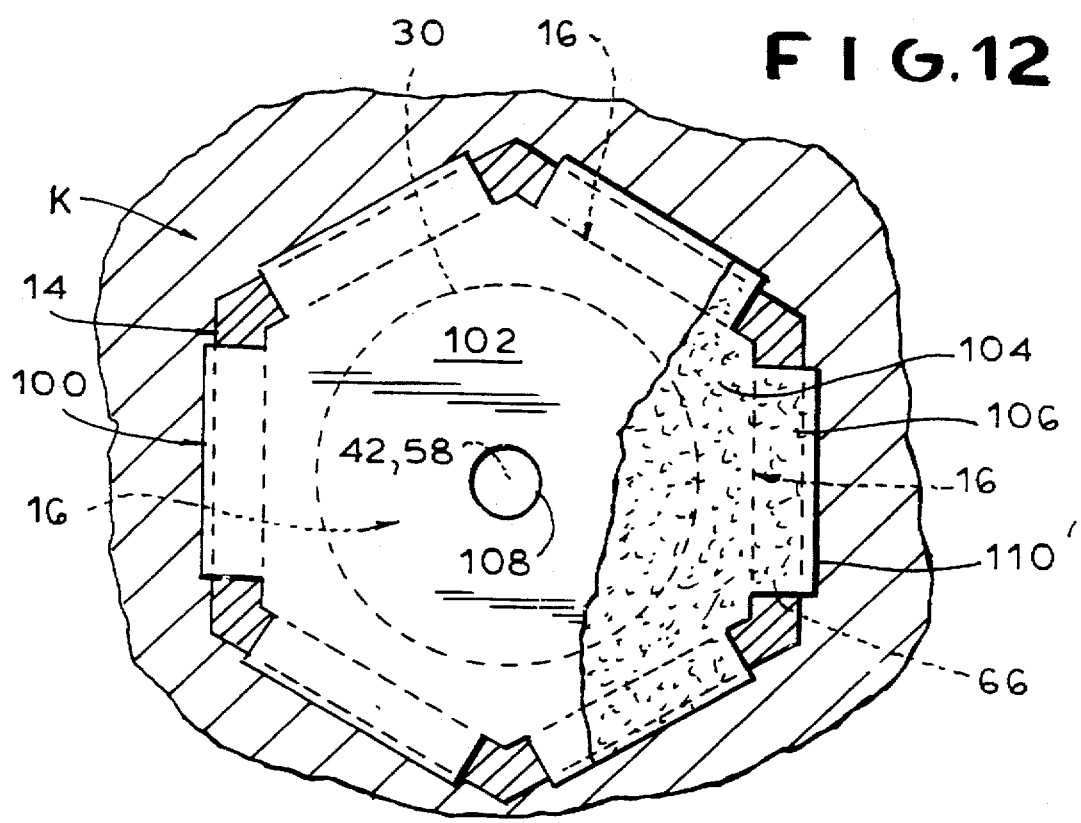
FIG. 12 is a fragmentary sectional view thereof taken along line 12—12 of FIG. 11.

The delivery unit cavity can be filled by varying amounts of the insert 16 in order to achieve a 5 flat or proud (convex) upper surface, and the body portion 104 of the fabric piece 102 can, if desired, be at least partially pre-shaped by conventional weaving techniques in order to achieve a corresponding surface (whether flat or convex). Purely for expository purposes, FIG. 11 shows the upper surface of fabric piece 102 and the top of the inserted insert 16 as they would be if the free ends 110 of the leg portions 106 on one side of the delivery unit 14 (the right side) were pulled more strongly than those on the other side (the left side). irregular contours are proud or upwardly projecting (over the top of delivery unit 14) on the left side and depressed or recessed (below the top of delivery unit 14) on the right side, presumably to best fill the removed portion of destroyed or damaged cartilage.

Assembly of the improved cartilage repair system is very simple. The surgeon (or surgical nurse) directly inserts the deformable insert 16 into the open-topped cavity of the delivery unit 14 so as to leave a top of the insert 16 exposed. As earlier noted, the upper surface contour of the insert top can be determined, to some degree, by the amount of insert placed into the cavity. Referring now to FIG. 9, the felt-like flexible, porous fabric piece 102 is then applied over the exposed top of the inserted insert 16 and through a plurality (preferably all) of the windows 66 of the sidewall of the delivery unit 14. The free end 110 of each leg portion 106 is then pulled, (or here the equivalent, pushed) through a respective window 66. For this reason, the free end 110 typically terminates in a point, thereby facilitating entry of the leg portion free end 110 through the respective window 66.

Then substantially all of each leg portion 102 is pulled through the respective window 66 to cause the body portion 104 to deform the inserted insert 16 into assuming the shape of the cavity therebelow. The pulling motion on each leg portion 106 assures that at least a portion of the inserted insert 16 will be frictionally pulled, with each leg portion free end 110, up to and through the respective window 66. The pulling of substantially all of each leg portion 106 through a respective window 66 typically causes the body portion 104 to deform the exposed top of the inserted insert 16 and cause it to assume a desired shape, depending upon the amount of insert within the cavity and the relative strength with which the individual leg portions are pulled.

Finally, as illustrated in FIG. 10, the leg portions 110 projecting from the respective windows 66 are trimmed at their free ends 116 so that the remaining fabric piece 102, with the trimmed leg portions 110' extending typically about 1–2 mm beyond the respective windows, retains the inserted insert 16 within the delivery unit 14.

The aforementioned pre-implantation steps of insert insertion, fabric piece application, leg portion pulling and leg portion trimming may be conveniently performed by a surgical nurse, although the surgeon may wish to perform the leg portion pulling step himself to assure that the top surface of the inserted insert assumes a desired shape. While the desired shape of the top surface of the insert may be regular and easy to describe to a surgical nurse, in other instances a more complex and hard-to-describe shape may be desired. In this instance, the surgeon can pull substantially all of each leg portion through a respective window himself, pulling more or less of each leg portion through its respective window as may be necessary to cause the top of the inserted insert to assume the desired shape.

The ability of the surgeon to reconfigure the top of the inserted insert in the operating room after he has seen the future site of the repair system in the body simply by differential pulling of the leg portions represents a substantial advantage of the present invention. Nonetheless, there exist other techniques which may be used, either instead of or in addition thereto, for determining the shape of the top of the inserted insert. Thus, the central body portion 104 of the fabric piece 102 may be custom woven to assist in this function. As a result of the custom weaving, the thickness of the body portion may vary over the surface area so that it is thicker at some points and relatively thinner at other points. Or the custom weaving may result in a shaping of the central portion much as the weaving of a sock can provide a shape to a woven piece of fabric. Traction stitching—that is, the use of certain threads which result in preferential adhesion or physical carrying of the inserted insert with the threads—may be applied in a given pattern to the fabric piece—for example, from one leg portion to a diametrically opposed leg portion across the central portion. The traction thread may be secured to the fabric piece in any of a variety of ways including stitching, bioabsorbent adhesives, heat welding and the like.

To summarize, the present invention provides an improved multi-component cartilage repair system which enables a simple and rapid assembly of the various components, even at the last moment in the operating theater. The improved system enables the insert to be assembled in the delivery unit with the desired upper surface contour and with the insert extending to and through the windows of the delivery unit. The present invention also provides a method for assembling such an improved system.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

I claim:

1. A method of assembling a bio-absorbable cartilage repair system for regenerating damaged or destroyed articular cartilage on a surface of a bone by establishing a chondrogenic growth-supporting matrix between an area of damaged or destroyed articular cartilage that has been removed and an adjacent healthy area of articular cartilage and cancellous bone, the system comprising an assembly of:

(A) a dimensionally stable, ceramic-free, bio-absorbable delivery unit configured and dimensioned to be mounted in both an area of damaged or destroyed articular cartilage that has been removed and an adjacent healthy area of articular cartilage and cancellous bone; and (B) a deformable, ceramic-free, porous, bio-absorbable insert supported by and in the delivery unit and establishing communication between the removed area and the adjacent healthy area for a chondrogenic growth-supporting matrix;

the delivery unit having an open top, a bottom and a sidewall connecting said top and bottom, the sidewall defining a plurality of windows to which the insert extends to allow cellular migration to the sides of the insert by an adjacent healthy area of articular cartilage;

the method comprising the steps of:

(a) directly inserting the insert into a cavity in the delivery unit so as to leave a top of the insert exposed;

(b) applying a flexible, porous fabric piece consisting substantially of bio-absorbable material over the exposed top of the inserted insert and through a plurality of the windows of the delivery unit sidewall, the fabric piece including a central body portion configured and dimensioned to substantially cover the exposed top of the inserted insert and a plurality of leg portions extending outwardly from the body portion, the leg portions being configured and dimensioned to fit through the windows;

(c) pulling substantially all of each leg portion through a respective window to cause the body portion to deform the inserted insert into assuming the shape of the cavity therebelow; and (d) trimming the leg portions projecting from the windows;

whereby the remaining fabric piece retains the inserted insert within the delivery unit.

2. The method of claim 1 wherein in step (c) the pulling also causes the body portion to deform the exposed top of the inserted insert into assuming a desired shape.

3. In a bio-absorbable cartilage repair system for regenerating damaged or destroyed articular cartilage on a surface of a bone by establishing a chondrogenic growth-supporting matrix between an area of damaged or destroyed articular cartilage that has been removed and an adjacent healthy area of articular cartilage and cancellous bone, said system comprising an assembly of:

(A) a dimensionally stable, ceramic-free, bio-absorbable delivery unit defining an open top cavity and configured and dimensioned to be mounted in both an area of damaged or destroyed articular cartilage that has been removed and an adjacent healthy area of articular cartilage and cancellous bone; and (B) a deformable, ceramic-free, porous, bio-absorbable insert supported by and in said cavity of said delivery unit so as to leave a top of said insert exposed and establishing communication between the removed area and the adjacent healthy area for a chondrogenic growth-supporting matrix;

said delivery unit cavity having an open top, a bottom and a sidewall connecting said top and bottom, said sidewall defining a plurality of windows to which said insert extends to allow cellular migration to the sides of said insert by an adjacent healthy area of articular cartilage;

the improvement comprising:

a flexible, porous fabric piece consisting substantially of bio-absorbable material disposed over the exposed top of said insert and through a plurality of said windows of said delivery unit sidewall, said fabric piece including a central body portion configured and dimensioned to substantially cover said exposed top of said insert and a plurality of leg portions extending outwardly from said body portion, said leg portions having free ends extending through respective windows, said body portion assuming the shape of the cavity therebelow; whereby said fabric piece retains said insert within said delivery unit.

4. The repair system of claim 3 wherein said leg portions extend beyond said respective windows by 1–2 mm.

5. The repair system of claim 3 wherein said fabric piece is formed of fibers of a substantially bio-absorbable material which is the same as the bio-absorbable insert.

6. The repair system of claim 3 wherein said plurality of leg portions is equal in number to said plurality of windows.

7. The repair system of claim 3 wherein said fabric piece is spider-shaped.

8. The repair system of claim 3 wherein said body portion completely covers said exposed top of said insert.

9. A method of assembling a bio-absorbable cartilage repair system for regenerating damaged or destroyed articular cartilage on a surface of a bone by establishing a chondrogenic growth-supporting matrix between an area of damaged or destroyed articular cartilage that has been removed and an adjacent healthy area of articular cartilage and cancellous bone, the system comprising an assembly of:

(A) a bio-absorbable delivery unit configured and dimensioned to be mounted in both an area of damaged or destroyed articular cartilage that has been removed and an adjacent healthy area of articular cartilage and cancellous bone; and (B) a deformable, porous, bio-absorbable insert supported by the delivery unit and establishing communication between the removed area and the adjacent healthy area for a chondrogenic growth-supporting matrix;

the delivery unit having a support portion which supports the insert to allow cellular migration to the sides of the insert by an adjacent healthy area of articular cartilage;

the method comprising the steps of:

(a) directly placing the insert on the support portion of the delivery unit so as to leave a top of the insert exposed;

(b) applying a flexible, porous fabric piece consisting substantially of bio-absorbable material over the exposed top of the insert, the fabric piece including a central body portion configured and dimensioned to substantially cover the exposed top of the insert and a plurality of leg portions extending outwardly from the body portion; and (c) using the leg portions to secure the insert on the delivery unit.

10. The method of claim 9 wherein in step (c) the leg supporting portions are used to cause the body portion to deform the exposed top of the insert into assuming a desired shape.

11. The method of claim 9 wherein said fabric piece is formed of fibers of a substantially bio-absorbable material which is the same as the bio-absorbable insert.

12. The method of claim 9 wherein said body portion completely covers said exposed top of said insert.

13. The method of claim 9 wherein said fabric piece is about 95% voids by volume.

* * * * *